United States Patent
Kawakami et al.

(10) Patent No.: US 9,295,981 B2
(45) Date of Patent: Mar. 29, 2016

(54) METHOD FOR PRODUCING ESTER COMPOUND BY REACTING AN UNSATURATED ORGANIC COMPOUND AND A FORMIC ACID ESTER IN THE PRESENCE OF A CATALYST SYSTEM CONTAINING A RUTHENIUM COMPOUND, A COBALT COMPOUND AND A HALIDE SALT

(75) Inventors: Hiroyuki Kawakami, Ichihara (JP); Kenichi Tominaga, Ushiku (JP); Kazuhiko Sato, Tsukuba (JP)

(73) Assignees: HITACHI CHEMICAL COMPANY, LTD., Tokyo (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 1099 days.

(21) Appl. No.: 13/387,443

(22) PCT Filed: May 13, 2010

(86) PCT No.: PCT/JP2010/058103
§ 371 (c)(1),
(2), (4) Date: Jan. 27, 2012

(87) PCT Pub. No.: WO2011/013430
PCT Pub. Date: Feb. 3, 2011

(65) Prior Publication Data
US 2012/0123146 A1 May 17, 2012

(30) Foreign Application Priority Data
Jul. 31, 2009 (JP) ................................. 2009-179132

(51) Int. Cl.
C07C 67/347 (2006.01)
C07C 69/24 (2006.01)
B01J 31/20 (2006.01)
B01J 31/02 (2006.01)
B01J 37/04 (2006.01)
C07C 67/38 (2006.01)
C07C 69/75 (2006.01)
C07C 69/753 (2006.01)

(52) U.S. Cl.
CPC .......... B01J 31/0239 (2013.01); B01J 31/0237 (2013.01); B01J 31/20 (2013.01); B01J 37/04 (2013.01); C07C 67/38 (2013.01); B01J 31/0282 (2013.01); B01J 31/0284 (2013.01); B01J 2231/321 (2013.01); B01J 2531/821 (2013.01); B01J 2531/845 (2013.01); C07C 2101/14 (2013.01); C07C 2102/42 (2013.01)

(58) Field of Classification Search
CPC ................................ C07C 67/38; C07C 45/50
See application file for complete search history.

(56) References Cited

U.S. PATENT DOCUMENTS

| | | | |
|---|---|---|---|
| 4,431,593 A | * | 2/1984 | Jenck ...................... C07C 67/38 554/131 |
| 4,614,816 A | | 9/1986 | Drury et al. |
| 4,892,976 A | | 1/1990 | Cordier et al. |
| 5,194,676 A | * | 3/1993 | Castanet .................. C07C 67/38 560/232 |

FOREIGN PATENT DOCUMENTS

| | | |
|---|---|---|
| EP | 0 980 706 A1 | 2/2000 |
| EP | 2 474 519 A1 | 7/2010 |
| EP | 2 492 258 A1 | 8/2012 |
| JP | 56-133242 A | 10/1981 |
| JP | 59-104343 | 6/1984 |
| JP | 61-134335 | 6/1986 |
| JP | 1-100140 | 4/1989 |
| JP | 8-20557 | 1/1996 |

OTHER PUBLICATIONS

Suzuki et al. "Synthesis of malonic esters by the catalytic addition of methyl formate to α,β-unsaturated esters" J. Molec. Catal. 1995, 95, 129-133.*
Park et al. "Immobilized heterobimetallic Ru/Co nanoparticle-catalyzed Pauson—Khand-type reactions in the presence of pyridylmethyl formate" Chem. Commun. 2003, 15, 1898-1899.*
Morimoto et al. "Evolution of Carbonylation Catalysis: No Need for Carbon Monoxide" Angew. Chem. Int. Ed. 2004, 43, 5580-5588.*
Nahmed et al. "Ester Formation from Ruthenium Catalyzed Alkene-Alkyl Formate Reaction" J. Molec. Catal. 1990, 59, L15-L19.*
Keim et al. "Homogeneous Multimetallic Catalysts Part 9. Hydroformylation of Norbornene by Cobalt-Ruthenium Bimetallic Catalyst" J. Molec. Catal. 1989, 54, 95-101.*
Keim et al. "Catalytic Reactions of Methyl Formate with Olefins" J. Molec. Catal. 1989, 54, 95-101.*

(Continued)

*Primary Examiner* — Nyeemah A Grazier
*Assistant Examiner* — Amanda L Aguirre
(74) *Attorney, Agent, or Firm* — Fitch, Even, Tabin and Flannery LLP

(57) ABSTRACT

Disclosed is an effective method for producing an ester compound at a reaction temperature lower than that of conventional methods, and with a high yield, even when inexpensive formic acid ester is used as a starting material. A method for producing an ester compound, the method comprising the step of reacting an organic compound having at least one unsaturated carbon bond in the molecule, and a formic acid ester in the presence of a catalyst system containing: a ruthenium compound; a cobalt compound; and a halide salt.

17 Claims, 3 Drawing Sheets

(56) References Cited

OTHER PUBLICATIONS

Park et al. "Halide Ions as a Highly Efficient Promoter in the Ru-Catalyzed Hydroesterification of Alkenes and Alkynes" Org. Lett. 2006, 8, 4355-4358.*

Hidai, M. "Homogeneous Multimetallic Catalysts Part 6. Hydroformylation and Hydroesterification of Olefins by Homogeneous Cobalt-Ruthenium Bimetallic Catalysts" J. Mol. Catal. 1986, 35, 29-37.*

Taiwan Office Action of Appln. No. 99118155 dated Jul. 8, 2014 with English translation.

JP Search Report of EP 10804178.1 dated Jan. 9, 2013 in English.

CN office action of Appln. No. 201080034088.9 dated Sep. 5, 2013 with partial English translation.

JP office Action of Appln. No. 2011-524695 dated Oct. 1, 2013 with partial English translation.

Korean Office Action of Appln. No. 10-2012-7001563 dated Jul. 12, 2013 with partial English translation.

International Preliminary Report dated Feb. 23, 2012 of Appln. No. PCT/JP2010/058103 in English.

Masanobu Hidai et al., Homogeneous Multimetallic Catalysts Pasrt 6.* Hydroformylation and Hydroesterification of Olefins by Homogeneous Cobalt-Ruthenium Bimetallic Catalysts, Journal of Molecular Catalysis, 35, 1986, pp. 29-37.

El Mostafa Nahmed et al., Ester Formation from Ruthenium Catalyzed Alkene-Alkyl Formate Reaction, Journal of Molecular Catalysis, 59, 1990, pp. L15-L19.

P. Isnard et al., Transition Metal Catalysed Interaction of Ethylene and Alkyl Formates, Journal of Organometallic Chemistry, 256, 1983, pp. 135-139.

Noel Lugan et al., Promoter Effect of Chloride Ions on the Ruthenium-Catalyzed Hydroesterification of Ethylene with Methyl Formate, Design and Evaluation of New Poly-and Mononuclear Catalyst Precursors, Organometallics 1995, pp. 1712-1731, vol. 14, No. 4.

Teruyuki Kondo et al., [PPN] $[Ru_3H(CO)_{11}]/PCy_3$ Catalyzed Direct Addition of Formyl Compounds to Alkenes, Organometallics 1999, pp. 4123-4127, vol. 18, No. 20.

Sangwon Ko et al., A Novel Chelation-Assisted Hydroesterification of Alkenes via Ruthenium Catalysis, Journal American Chemical Society, 2002, pp. 750-751, Vo. 124, No. 5.

M. J. Cleare et al., Halogeno-carbonyl and —nitrosly Complexes of the Platinum Metals, and their Vibrational Spectra, Journal Chemical Society (A), 1969, pp. 372-380.

Office Action of Chinese Appln. No. 201080034088.9 dated Aug. 13, 2015 with English translation.

* cited by examiner

METHOD FOR PRODUCING ESTER COMPOUND BY REACTING AN UNSATURATED ORGANIC COMPOUND AND A FORMIC ACID ESTER IN THE PRESENCE OF A CATALYST SYSTEM CONTAINING A RUTHENIUM COMPOUND, A COBALT COMPOUND AND A HALIDE SALT

TECHNICAL FIELD

The present invention relates to a method for producing an ester compound using an organic compound having an unsaturated bond and a formic acid ester as raw materials. More particularly, the present invention relates to a method for producing an ester compound which is the organic compound with an added ester group, efficiently at a low temperature by reacting the raw materials in the presence of a particular catalyst system, without substantially using carbon monoxide as a raw material.

BACKGROUND ART

There are conventionally known various methods of and producing an ester compound which is the organic compound with an added ester group, by using an organic compound having an unsaturated bond and a formic acid compound as raw materials, without substantially using carbon monoxide.

For example, Non-Patent Literature 1 discloses a method for producing methyl propionate, which is a product of addition of methyl formate to ethylene, by reacting ethylene and methyl formate for 18 hours under the temperature conditions of 190° C., while using a ruthenium compound having a phosphine ligand as a catalyst. According to this disclosed method, methyl propionate is produced in an amount of 286 molar equivalents with respect to the ruthenium compound.

Non-Patent Literature 2 discloses a method for producing methyl propionate, which is a product of addition of methyl formate to ethylene, by reacting ethylene and methyl formate for 2 hours under the temperature conditions of 160° C. in DMF solvent, while using a ruthenium compound having a carbonyl ligand and a chlorine ligand as a catalyst. According to this disclosed method, methyl propionate is produced in an amount of 345 molar equivalents with respect to the ruthenium compound.

Patent Literature 1 discloses a method for producing methyl propionate by reacting ethylene and methyl formate to react for one hour under the temperature conditions of 190° C. in DMF solvent and in the presence of a catalyst system composed of a ruthenium compound having a ligand selected from the group consisting of a carbonyl ligand, a chlorine ligand and an amine ligand, and a quaternary ammonium iodide. According to this disclosed method, methyl propionate is produced in an amount of 1530 molar equivalents with respect to the ruthenium compound.

Non-Patent Literature 3 discloses a method for producing a compound which is norbornene with an added ester group, by reacting norbornene and methyl formate for 15 hours under the temperature conditions of 170° C. in toluene, while using a combination of a ruthenium carbonyl cluster compound and a tertiary phosphine compound as a catalyst. According to this disclosed method, the compound which is norbornene with an added ester group is obtained at a yield of 22% in terms of methyl formate. Furthermore, when benzyl formate is used instead of methyl formate, the corresponding ester compound is obtained at a yield of 77%.

Non-Patent Literature 4 discloses a method of reacting 1-hexene and a formic acid compound having a pyridine group for 4 hours under the temperature conditions of 135° C. in DMF solvent, while using a ruthenium carbonyl cluster compound as a catalyst, and thereby producing a corresponding ester compound. According to this disclosed method, the ester compound is obtained at a yield of 98% in terms of the formic acid compound.

The various methods described above are highly useful as methods for producing a desired ester compound from an organic compound having an unsaturated bond, even among a variety of methods for producing ester compounds, since the use of toxic raw materials such as carbon monoxide is unnecessary, and the reaction proceeds at a relatively low pressure.

CITATION LIST

Patent Literatures

Patent Literature 1: Japanese Patent Application Laid-Open (JP-A) No. Hei 8-20557

Non-Patent Literatures

Non-Patent Literature 1: P. Isnard, B. Denise, R. P. A. Sneeden, J. M. Cognion, P. Durual, J. Organomet. Chem., 256, 135 (1983)

Non-Patent Literature 2: N. Lugan, G Lavigne, J. M. Soulie, S. Fabre, P. Kalck, J. Y. Saillard, J. F. Halet, Organometallics, 14, 1712 (1995)

Non-Patent Literature 3: T. Kondo, T. Okada, T. Mitsudo, Organometallics, 18, 4123 (1999)

Non-Patent Literature 4: S. KO, Y. Na, S. Chang, J. Am. Chem. Soc., 124, 750 (2002)

Non-Patent Literature 5: M. J. Cleare, W. P. Griffith, J. Chem. Soc. (A), 1969, 372

SUMMARY OF THE INVENTION

Technical Problem

However, in order to produce ester compounds with a high yield by applying the various methods described above while using the most inexpensive methyl formate as a formic acid ester, a high reaction temperature such as 160° C. or higher is required. Furthermore, in order to produce ester compounds with a high yield at a reaction temperature lower than 160° C., it is needed to use a special formic acid compound having a pyridine group or the like as the formic acid ester.

An object of the present invention is to provide a method for producing an ester compound which is a raw material organic compound with an added ester group, using an unsaturated organic compound and a formic acid ester as raw materials, without using a substantial amount of carbon monoxide. Particularly, it is an object of the present invention to provide a method for producing a desired ester compound at a reaction temperature lower than that of conventional methods, and with a high yield, even when inexpensive methyl formate is used as the formic acid ester.

Solution to Problem

Under such circumstances as described above, the inventors of the present invention conducted a thorough investigation. As a result, the inventors found that when an unsaturated organic compound and a formic acid ester are reacted in the presence of a catalyst system containing: a ruthenium compound; a cobalt compound; and a halide salt, the reaction proceeds at a temperature lower than the reaction temperature required in conventional methods, and a desired ester compound is obtained with a high yield, thus completing the present invention. That is, the feature of the present invention relates to the items described below.

The method for producing an ester compound according to the present invention is characterized by reacting an organic compound having at least one unsaturated carbon bond in the molecule, and a formic acid ester to react in the presence of a catalyst system containing: a ruthenium compound; a cobalt compound; and a halide salt.

Here, in regard to the production method described above, the ruthenium compound is preferably a ruthenium complex having both a carbonyl ligand and a halogen ligand in the molecule. The cobalt compound is preferably a cobalt complex having a carbonyl ligand in the molecule. Furthermore, the halide salt is preferably a quaternary ammonium salt.

It is preferable that the reaction be carried out in the presence of a basic compound. The basic compound is preferably a tertiary amine compound. Furthermore, it is preferable that the reaction be carried out in the presence of a phenolic compound. It is preferable that the reaction be carried out in the presence of an organic halogen compound. In regard to the reaction described above, two or more compounds selected from the group consisting of the basic compound, the phenolic compound and the organic halogen compound may be used in combination.

Advantageous Effects of Invention

According to the present invention, a desired ester compound can be efficiently produced through a one-step reaction using inexpensive raw materials, without a need to use toxic raw materials such as carbon monoxide or a special apparatus. The method according to the present invention can be realized with less capital investments, and the environmental impact can also be suppressed to a minimal level. Therefore, the method of the present invention can sufficiently cope with the needs of industry.

Meanwhile, the present patent application claims priority based on Japanese Patent Application No. 2009-179132 filed on Jul. 31, 2009, by the same Applicant, the disclosure of which is incorporated as a part of the present specification by reference.

DESCRIPTION OF EMBODIMENTS

Figure 1:
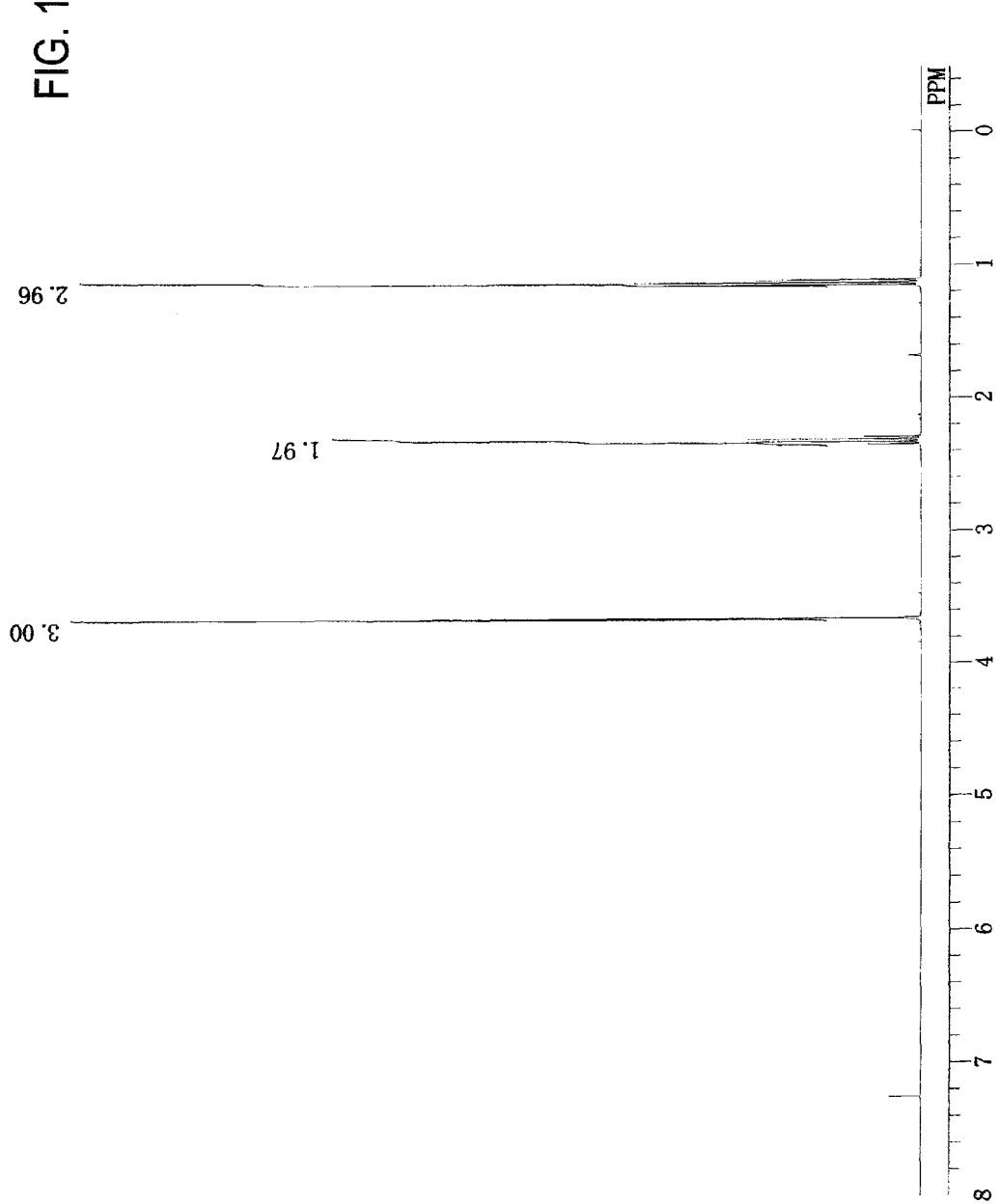
FIG. 1 is the 1H-NMR spectrum of methyl propionate obtained in Example 1.

Hereinafter, the present invention will be described in more detail. An embodiment of the present invention relates to a method for producing an ester compound by reacting an organic compound having at least one unsaturated carbon bond in the molecule (hereinafter, referred to as "unsaturated organic compound") and a formic acid ester in the presence of a catalyst system containing: a ruthenium compound; a cobalt compound; and a halide salt.

(Unsaturated Organic Compound)

The unsaturated organic compound that can be used as a raw material in the present invention may be any compound having one or more unsaturated carbon bonds in the molecule, and there are no particular limitations. That is, the unsaturated organic compound may be any one of various compounds including aliphatic linear unsaturated compounds, aliphatic cyclic unsaturated compounds, and aromatic compounds. Here, the unsaturated carbon bond may be present at the ends of the molecular chain, or may be present internally in the molecular chain. Furthermore, the unsaturated organic compound may also be a compound having plural unsaturated carbon bonds in the molecule. When a compound having plural unsaturated carbon bonds in the molecule is used as the raw material, it is possible to produce a compound having plural ester groups in the molecule.

Specific examples of the aliphatic linear unsaturated compounds include ethylene, propylene, butylene, pentene, hexane, heptene, octane, nonene, decene, undecene, dodecene, tridecene, tetradecene, pentadecene, hexadecene, heptadecene, octadecene, nonadecene, butadiene, pentadiene, hexadiene, heptadiene, octadiene, nonadiene, hexanetriene, heptatriene, octatriene, and isomers and derivatives thereof.

Specific examples of the aliphatic cyclic unsaturated compounds include cyclopentene, cyclohexene, cycloheptene, cyclooctene, cyclopentadiene, cyclohexadiene, cycloheptadiene, cyclooctadiene, tetrahydroindene, methyltetrahydroindene, norbornene, norbornadiene, methylvinylnorbornene, dicyclopentadiene, methyldicyclopentadiene, tricyclopentadiene, tetracyclopentadiene, norbornene, norbornadiene, and isomers and derivatives thereof.

The aromatic compounds include aromatic linear unsaturated compounds and aromatic cyclic unsaturated compounds. Specific examples of the aromatic linear unsaturated compounds include styrene, stilbene, triphenylethylene, tetraphenylethylene, and derivatives thereof. Examples of the aromatic cyclic unsaturated compounds include indene, dihydronaphthalene, indole, and derivatives thereof.

The unsaturated organic compound described above may have the hydrogen atoms in the molecule substituted with one or more functional groups selected from the group consisting of an alkyl group, a cyclic aliphatic group, an aromatic group, a heterocyclic group, a carbonyl group, a carboxylic acid group, an ester group, an alkoxy group, a cyano group, an amino group, an amide group, a nitro group, a halogen, and a phosphorus-containing substituent. There are no particular limitations, but examples of such a compound include methyl norbornene dicarboxylate, and methyl norbornene carboxylate.

(Formic Acid Ester)

There are no particular limitations on the formic acid ester that can be used as a raw material in the present invention. For example, the formic acid ester can be appropriately selected for use from the group consisting of methyl formate, ethyl formate, propyl formate, isopropyl formate, butyl formate, isobutyl formate, amyl formate, isoamyl formate, allyl formate, vinyl formate, benzyl formate, and the like. From the viewpoints of cost and reactivity, methyl formate is suitable.

According to the present invention, a catalyst system which essentially contains three components such as a ruthenium compound, a cobalt compound and a halide salt, is used. As will be made clear in the Examples that will be described below, in the present invention, the predefined purpose can be achieved by a particular combination of a ruthenium compound, a cobalt compound and a halide salt. It is not intended to be bound by theory, but it can be speculated that the esterification reaction of the unsaturated organic compound according to the present invention proceeds as the ruthenium compound cleaves the C—H bond of the formic acid ester, and the unsaturated bond of the unsaturated compound reacts with the added cobalt compound, while such a reaction is accelerated by the halide salt. Hereinafter, the various compounds will be specifically described.

(Ruthenium Compound)

The ruthenium compound that can be used in the present invention may be any compound containing ruthenium, and there are no particular limitations. For example, there may be mentioned a ruthenium complex compound having a structure in which a ruthenium atom at the center is bonded to a surrounding array of ligands. According to an embodiment of the present invention, a ruthenium compound having both a carbonyl ligand and a halogen ligand in the molecule is preferred. Specific examples of such a ruthenium compound include $[RuCl_2(CO)_3]_2$, $[RuCl_2(CO)_2]_n$, and various compounds having $[Ru(CO)_3Cl_3]^-$, $[Ru_3(CO)_{11}Cl]^-$ and $[Ru_4(CO)_{13}Cl]^-$ as counteranions. It is preferable that the various compounds having the above-mentioned counteranions have, for example, metal ions of alkali metals, alkaline earth metals and the like as countercations. Among the exemplified compounds, $[Ru(CO)_3Cl_2]_2$ and $[Ru(CO)_2Cl_2]_n$ are more preferred from the viewpoint of enhancing the reaction ratio.

The ruthenium compound used in the present invention can be produced according to a method well known in the pertinent art, but the ruthenium compound can also be purchased as a commercial product. Furthermore, $[Ru(CO)_2Cl_2]_n$ can be produced according to the method described in M. J. Cleare, W. P. Griffith, J. Chem. Soc. (A), 1969, 372 (Non-Patent Literature 5).

In regard to the ruthenium compound used in the present invention, the ruthenium compounds described above may be produced before or during the esterification reaction according to the present invention, for example, using $RuCl_3$, $Ru_3(CO)_{12}$, $RuCl_2(C_8H_{12})$, $Ru(CO)_3(C_8H_8)$, $Ru(CO)_3(C_8H_{12})$, and $Ru(C_8H_{10})(C_8H_{12})$ as precursor compounds, and the produced ruthenium compounds may be introduced into the reaction system.

When the production cost is considered, it is preferable to use the ruthenium compound in an amount as small as possible. However, if the use amount of the ruthenium compound is less than 1/10000 equivalents, the rate of the esterification reaction tends to extremely decrease. Accordingly, the use amount of the ruthenium compound is preferably in the range of 1/10000 to 1 equivalent, and more preferably in the range of 1/1000 to 1/50 equivalents, based on the unsaturated organic compound that is used as a raw material.

(Cobalt Compound)

The cobalt compound that can be used in the present invention may be any compound containing cobalt, and there are no particular limitations. Specific examples of suitable compounds include cobalt compounds having a carbonyl ligand, such as $Co_2(CO)_8$, $HCo(CO)_4$ and $Co_4(CO)_{12}$; cobalt compounds having a carboxylic acid compound as a ligand, such as cobalt acetate, cobalt propionate, cobalt benzoate and cobalt citrate; and cobalt phosphate. Among them, cobalt complex compounds having a carbonyl ligand are preferred from the viewpoint of enhancing the reaction ratio.

The use amount of the cobalt compound is in the range of 1/100 to 10 equivalents, and preferably 1/10 to 5 equivalents, based on the ruthenium compound. If the ratio of the cobalt compound to the ruthenium compound is lower than 1/100 equivalents, or if the ratio is higher than 10 equivalents, the amount of the ester compound produced tends to significantly decrease.

(Halide Salt)

The halide salt that can be used in the present invention may be any compound composed of a halogen ion such as a chloride ion, a bromide ion or an iodide ion, and a cation, and there are no particular limitations. The cation may be any of an inorganic ion and an organic ion. Furthermore, the halide salt may contain one or more halogen ions in the molecule.

The inorganic ion that constitutes the halide salt may be a metal ion selected from alkali metals and alkaline earth metals. Specific examples thereof include lithium, sodium, potassium, rubidium, cesium, calcium, and strontium.

Furthermore, the organic ion may be a monovalent or higher-valent organic group derived from an organic compound. Examples thereof include ammonium, phosphonium, pyrrolidinium, pyridium, imidazolium, and iminium, and the hydrogen atoms of these ions may be substituted by hydrocarbon groups such as alkyl and aryl. There are no particular limitations, but specific examples of suitable organic ions include tetramethylammonium, tetraethylammonium, tetrapropylammonium, tetrabutylammonium, tetrapentylammonium, tetrahexylammonium, tetraheptylammonium, tetraoctylammonium, trioctylmethylammonium, benzyltrimethylammonium, benzyltriethylammonium, benzyltributylammonium, tetramethylphosphonium, tetraethylphosphonium, tetraphenylphosphonium, benzyltriphenylphosphonium, and bis(triphenylphosophine)iminium. Among them, from the viewpoint of enhancing the reaction ratio, quaternary ammonium salts such as butylmethylpyrrolidinium chloride, bis(triphenylphosphine)iminium iodide and trioctylmethylammonium chloride are more preferred.

The halide salt used in the present invention is not necessarily a solid salt, and an ionic liquid containing a halide ion, which becomes liquid at near room temperature or in a temperature region of 100° C. or lower, may also be used. Specific examples of the cation used in such an ionic liquid include organic ions such as 1-ethyl-3-methylimidazolium, 1-propyl-3-methylimidazolium, 1-butyl-3-methylimidazolium, 1-pentyl-3-methylimidazolium, 1-hexyl-3-methylimidazolium, 1-heptyl-3-methylimidazolium, 1-octyl-3-methylimidazolium, 1-decyl-3-methylimidazoium, 1-dodecyl-3-methylimidazoium, 1-tetradecyl-3-methylimidazoium, 1-hexadecyl-3-methylimidazoium, 1-octadecyl-3-methylimidazoium, 1-ethyl-2,3-dimethylimidazoium, 1-butyl-2,3-dimethylimidazolium, 1-hexyl-2,3-dimethylimidazoium, 1-ethylpyridinium, 1-butylpyridinium, 1-hexylpyridinium, 8-methyl-1,8-diazabicyclo[5.4.0]-7-undecene, 8-ethyl-1,8-diazabicyclo[5.4.0]-7-undecene, 8-propyl-1,8-diazabicyclo[5.4.0]-7-undecene, 8-butyl-1,8-diazabicyclo[5.4.0]-7-undecene, 8-pentyl-1,8-diazabicyclo[5.4.0]-7-undecene, 8-hexyl-1,8-diazabicyclo[5.4.0]-7-undecene, 8-heptyl-1,8-diazabicyclo[5.4.0]-7-undecene, and 8-octyl-1,8-diazabicyclo[5.4.0]-7-undecene. In the present invention, the halide salts described above may be used singly, or may be used in combination of a plurality thereof.

Among the halide salts described above, suitable halide salts are chloride salts, bromide salts and iodide salts, in which the cation is an organic ion. There are no particular limitations, but specific examples of suitable halide salts for the present invention include butylmethylpyrrolidinium chloride, bis(triphenylphosphine)iminium iodide, and trioctylmethylammonium chloride.

The addition amount of the halide salt is, for example, in the range of 1 to 1000 equivalents, and preferably 2 to 50 equivalents, based on the ruthenium compound. When the addition amount is adjusted to 1 equivalent or more, the rate of reaction can be effectively increased. On the other hand, when the addition amount exceeds 1000 equivalents, there is a tendency that even if the addition amount is further increased, an effect of further enhancing the acceleration of the reaction may not be obtained.

In the production method according to the present invention, when a basic compound, a phenolic compound or an organic halogen compound is added as necessary to a particular catalyst system containing: a ruthenium compound; a cobalt compound; and a halide salt, the effect of accelerating the reaction by means of the catalyst system can be further increased. Hereinafter, the various compounds will be explained.

(Basic Compound)

According to the present invention, the effect of accelerating the reaction by means of a basic compound may vary with the type of the unsaturated organic compound that is used as a raw material. The basic compound that can be used for the present invention may be an inorganic compound or may be an organic compound. Specific examples of a basic inorganic compound include carbonates, hydrogen carbonates, hydroxide salts, and alkoxides of various metals such as alkali metals and alkaline earth metals. Specific examples of a basic organic compound include primary amine compounds, secondary amine compounds, tertiary amine compounds, pyridine compounds, imidazole compounds, and quinoline compounds. Among the basic compounds described above, tertiary amine compounds are suitable from the viewpoint of the effect of accelerating the reaction. Specific examples of tertiary amine compounds suitable for the present invention include trialkylamine, N-alkylpyrrolidine, N-alkylpiperidine, quinucridine, and triethylenediamine.

The addition amount of the basic compound is not particularly limited, but for example, the addition amount is in the range of 1 to 1000 equivalents, and preferably 2 to 200 equivalents, based on the ruthenium compound. When the addition amount is adjusted to 1 equivalent or more, the manifestation of the accelerating effect tends to become more conspicuous. Furthermore, when the addition amount exceeds 1000 equivalents, there is a tendency that even if the addition amount is further increased, an effect of further enhancing the acceleration of the reaction may not be obtained.

(Phenolic Compound)

According to the present invention, the effect of accelerating the reaction by adding a phenolic compound may vary with the type of the unsaturated organic compound that is used as a raw material. Specific examples of suitable phenolic compounds for the present invention include phenol, cresol, alkylphenol, methoxyphenol, phenoxyphenol, chlorophenol, trifluoromethylphenol, hydroquinone, and catechol.

The addition amount of the phenolic compound is, for example, in the range of 1 to 1000 equivalents, and preferably 2 to 50 equivalents, based on the ruthenium compound. When the addition amount is adjusted to 1 equivalent or more, the manifestation of the accelerating effect tends to become more conspicuous. Furthermore, when the addition amount exceeds 1000 equivalents, there is a tendency that even if the addition amount is further increased, an effect of further enhancing the acceleration of the reaction may not be obtained.

(Organic Halogen Compound)

According to the present invention, the effect of accelerating the reaction by adding an organic halogen compound may vary with the type of the unsaturated organic compound that is used as a raw material. Examples of suitable organic halogen compounds for the present invention include methyl halide, dihalogenmethane, dihalogenethane, trihalogenmethane, carbon tetrahalide, and benzene halide.

The addition amount of the organic halogen compound is, for example, in the range of 1 to 1000 equivalents, and preferably 2 to 50 equivalents, based on the ruthenium compound. When the addition amount is adjusted to 1 equivalent or more, the manifestation of the accelerating effect tends to become conspicuous. Furthermore, when the addition amount exceeds 1000 equivalents, there is a tendency that even if the addition amount is further increased, an effect of further enhancing the acceleration of the reaction may not be obtained.

(Solvent)

In the production method of the present invention, the reaction of the unsaturated organic compound and the formic acid ester can be carried out without particularly using a solvent. However, a solvent may be used if necessary. The solvent that can be used for the present invention is not particularly limited as long as the solvent is capable of dissolving the compounds used as the raw materials. Specific examples of solvents that can be suitably used for the present invention include n-pentane, n-hexane, n-heptane, cyclohexane, benzene, toluene, o-xylene, p-xylene, m-xylene, ethylbenzene, cumene, tetrahydrofuran, N-methylpyrrolidone, dimethylformamide, dimethylacetamide, dimethylimidazolidinone, ethylene glycol dimethyl ether, diethylene glycol dimethyl ether, and triethylene glycol dimethyl ether.

(Reaction Temperature)

In the production method of the present invention, the reaction of the unsaturated organic compound and the formic acid ester is preferably carried out at a temperature in the range of 80° C. to 200° C. It is more preferable that the reaction be carried out at a temperature in the range of 100° C. to 160° C. When the reaction is carried out at a temperature of 80° C. or higher, the rate of reaction is increased, and the reaction can be efficiently carried out. On the other hand, when the reaction temperature is controlled to be 200° C. or lower, the decomposition of the formic acid ester that is used as a raw material can be prevented. When the formic acid ester is decomposed, the addition of an ester group to the unsaturated organic compound is not achieved, and therefore, an excessively high reaction temperature is not desirable. When the reaction temperature is higher than the boiling point of any of the unsaturated organic compound and the formic acid ester that are used as the raw materials, the reaction needs to be carried out in a pressure-resistant vessel. The completion of the reaction can be confirmed by using well known analytic technologies such as gas chromatography and NMR.

EXAMPLES

Hereinafter, the present invention will be described in more detail by way of Examples. However, the scope of the present invention is not intended to be limited by the following Examples.

Example 1

Addition of Methyl Formate to Ethylene

In a pressure reactor made of stainless steel and having an internal volume of 50 ml, 0.05 mmol of $[Ru(CO)_3Cl_2]_2$ as a ruthenium compound, 0.05 mmol of $Co_2(CO)_8$ as a cobalt compound, and 1.0 mmol of butylmethylpyrrolidinium chloride as a halide salt were introduced and mixed at room temperature, and thus a catalyst system was obtained. 5.0 mL of methyl formate was added to this catalyst system, subsequently ethylene gas was injected into the reactor to 2 MPa, and the system was maintained for 15 hours at 120° C. Thereafter, the reactor was cooled to room temperature, and the pressure was released. A portion of the remaining organic phase was withdrawn, and the components of the reaction mixture were analyzed by using gas chromatography. According to the analysis results, the amount of methyl propionate produced by the reaction was 24.2 mmol (242 equivalents in terms of ruthenium atoms).

The conditions for the analysis by gas chromatography are as follows.

Apparatus: GC-353B type GC manufactured by GL Sciences, Inc.
Detector: Hydrogen flame ionization detector
Column: TC-1 (60 m) manufactured by GL Sciences, Inc.
Carrier gas: Helium (300 kPa)
Temperature: Inlet port 200° C.; detector 200° C.; column 40° C. to 240° C. (rate of temperature increase 5° C./min)

The 1H-NMR spectrum of methyl propionate obtained as a product is presented in FIG. 1. The measurement conditions for the 1H-NMR spectrum shown in FIG. 1, and the identification data are as follows.

Conditions: Solvent DMSO-d6, apparatus "AV400M" manufactured by Bruker Corporation (proton fundamental frequency: 400.13 MHz).

Data: Near 1.2 ppm, methyl group of the propionate moiety; near 2.4 ppm, methylene group of the propionate moiety; and near 3.7 ppm, methyl group of the methyl ester moiety.

Comparative Example 1

Catalyst System Consisting of Ruthenium Compound and Halide Salt Only

The reaction was carried out under the same conditions as in Example 1, except that the cobalt compound used in the catalyst system of Example 1 was not used. The reaction mixture thus obtained was analyzed in the same manner as in Example 1, and the amount of methyl propionate produced by the reaction was 8.1 mmol (81 equivalents in terms of ruthenium atoms).

Comparative Example 2

Catalyst System Consisting of Cobalt Compound and Halide Salt Only

The reaction was carried out all under the same conditions as in Example 1, except that the ruthenium compound used in the catalyst system of Example 1 was not used. The components of the reaction mixture thus obtained were analyzed by gas chromatography, and only a trace amount of methyl propionate was produced by the reaction.

Comparative Example 3

Catalyst System Consisting of Ruthenium Compound and Cobalt Compound Only

The reaction was carried out all under the same conditions as in Example 1, except that the halide salt used in the catalyst system of Example 1 was not used. The reaction mixture thus obtained was analyzed by gas chromatography, and only a trace amount of methyl propionate was produced by the reaction.

Example 2

Addition of Methyl Formate to Cyclohexene

In a pressure reactor made of stainless steel and having an internal volume of 50 ml, 0.05 mmol of $[Ru(CO)_3Cl_2]_2$ as a ruthenium compound, 0.05 mmol of $Co_2(CO)_8$ as a cobalt compound, and 1.0 mmol of [bis(triphenylphosphine)iminium]iodide as a halide salt were introduced and mixed at room temperature, and thus a catalyst system was obtained. 5.0 mmol of cyclohexene and 5.0 mL of methyl formate were added to this catalyst system, subsequently the reactor was purged with nitrogen gas at 0.5 MPa, and the system was maintained for 15 hours at 120° C. Thereafter, the reactor was cooled to room temperature, and the pressure was released. A portion of the remaining organic phase was withdrawn, and the components of the reaction mixture were analyzed by using gas chromatography. According to the analysis results, the amount of methyl cyclohexanecarboxylate produced by the reaction was 2.47 mmol (yield in terms of cyclohexene 49.4%).

Figure 2:
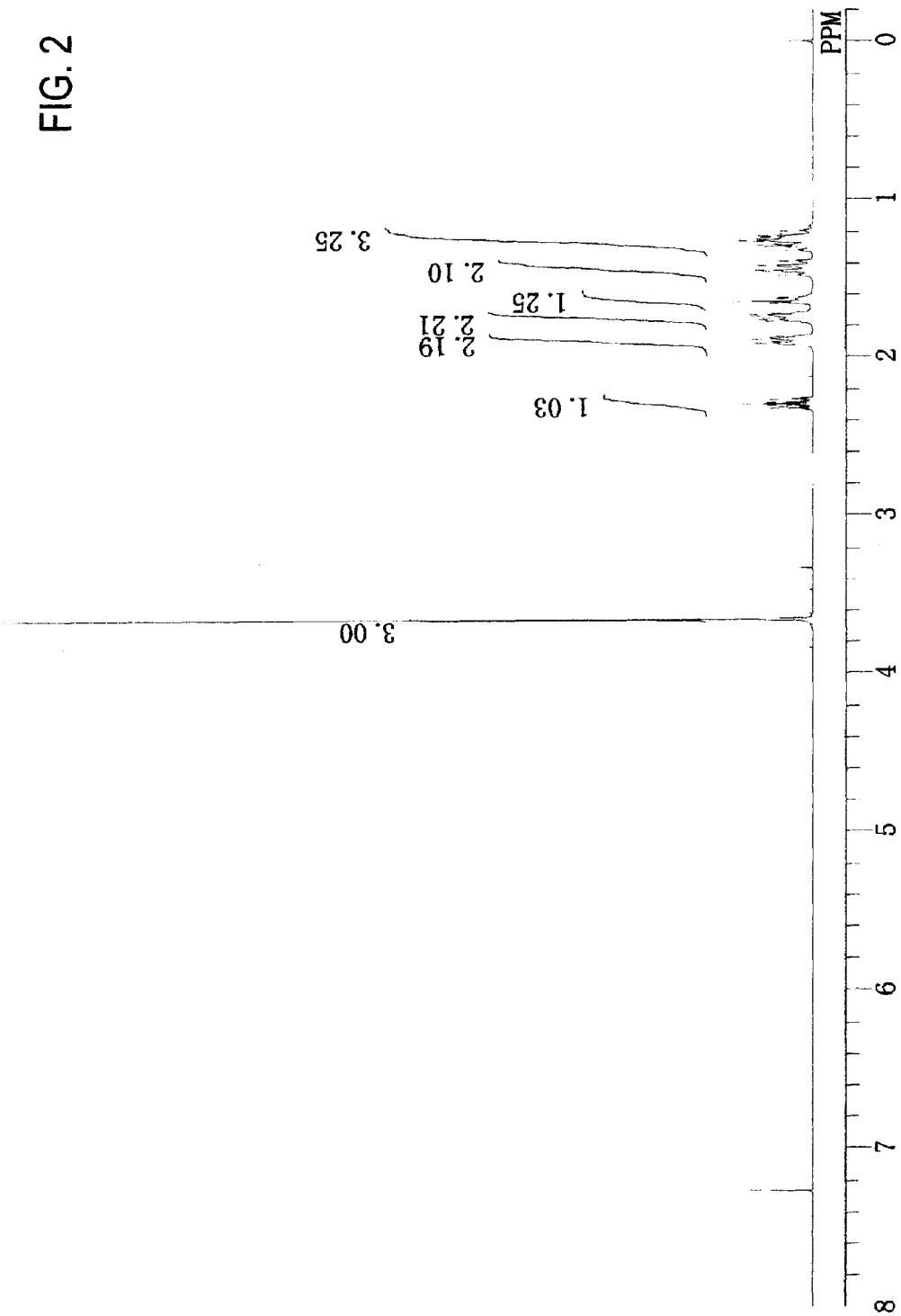
FIG. 2 is the 1H-NMR spectrum of methyl cyclohexanecarboxylate obtained in Example 2.

The 1H-NMR spectrum of methyl cyclohexanecarboxylate obtained as a product is presented in FIG. 2. The measurement conditions for the 1H-NMR spectrum shown in FIG. 2, and the identification data are as follows.

Conditions: Solvent DMSO-d6, apparatus "AV400M" manufactured by Bruker Corporation (proton fundamental frequency: 400.13 MHz).

Data: Near 1.2 to 2.3 ppm, cyclohexane ring; and near 3.7 ppm, methyl group of the methyl ester moiety.

Example 3

Addition of Methyl Formate to Methyl Norbornene Dicarboxylate

In a pressure reactor made of stainless steel and having an internal volume of 50 ml, 0.025 mmol of $[Ru(CO)_3Cl_2]_2$ as a ruthenium compound, 0.025 mmol of $Co_2(CO)_8$ as a cobalt compound, and 0.5 mmol of butylmethylpyrrolidinium chloride as a halide salt were introduced and mixed at room temperature, and thus a catalyst system was obtained. 10.0 mmol of methyl 5-norbornene-2,3-dicarboxylate and 5.0 mL of methyl formate were added to this catalyst system, subsequently the reactor was purged with nitrogen gas at 0.5 MPa, and the system was maintained for 15 hours at 120° C. Thereafter, the reactor was cooled to room temperature, and the pressure was released. A portion of the remaining organic phase was withdrawn, and the components of the reaction mixture were analyzed by using gas chromatography. According to the analysis results, the amount of methyl norbornane-2,3,5-tricarboxylate produced by the reaction was 0.84 mmol (yield in terms of methyl 5-norbornene-2,3-dicarboxylate 8.4%).

Figure 3:
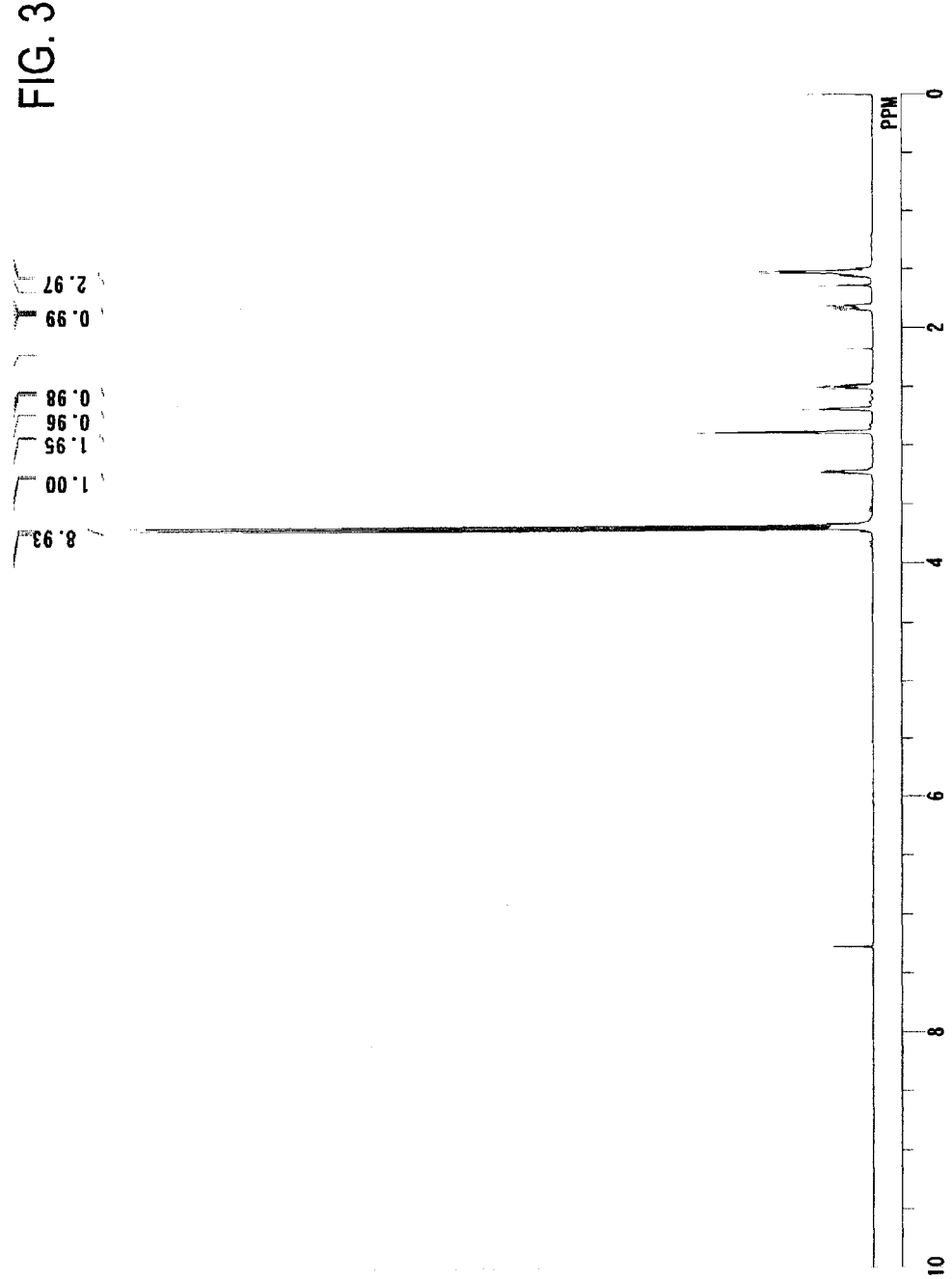
FIG. 3 is the 1H-NMR spectrum of methyl norbornane-2,3,5-tricarboxylate obtained in Example 3.

The 1H-NMR spectrum of methyl norbornane-2,3,5-tricarboxylate obtained as a product is presented in FIG. 3. The measurement conditions for the 1H-NMR spectrum shown in FIG. 3, and the identification data are as follows.

Conditions: Solvent DMSO-d6, apparatus "AV400M" manufactured by Bruker Corporation (proton fundamental frequency: 400.13 MHz).

Data: Near 1.5 to 3.2 ppm, norbornane ring; and near 3.7 ppm, methyl group of the methyl ester moiety.

Example 4

Addition of Methyl Formate to Methyl Norbornene Dicarboxylate

The reaction was carried out all under the same conditions as in Example 3, except that 2.0 mmol of N-methylpyrrolidine was added as a basic compound to the catalyst system used in Example 3. The reaction mixture thus obtained was analyzed by gas chromatography, and the amount of methyl norbornane-2,3,5-tricarboxylate produced by the reaction was 1.11 mmol (yield in terms of methyl 5-norbornene-2,3-dicarboxylate 11.1%).

Example 5

Addition of Methyl Formate to Methyl Norbornene Dicarboxylate

The reaction was carried out all under the same conditions as in Example 3, except that 0.5 mmol of sodium t-butoxide was added as a basic compound to the catalyst system used in Example 3. The reaction mixture thus obtained was analyzed by gas chromatography, and the amount of methyl norbornane-2,3,5-tricarboxylate produced by the reaction was 3.08 mmol (yield in terms of methyl 5-norbornene-2,3-dicarboxylate 30.8%).

Example 6

Addition of Methyl Formate to Methyl Norbornene Dicarboxylate

The reaction was carried out all under the same conditions as in Example 3, except that 2.0 mmol of N-methylpyrrolidine as a basic compound and 0.5 mmol of p-cresol as a phenolic compound were added to the catalyst system used in Example 3. The reaction mixture thus obtained was analyzed by gas chromatography, and the amount of methyl norbornane-2,3,5-tricarboxylate produced by the reaction was 8.97 mmol (yield in terms of methyl 5-norbornene-2,3-dicarboxylate 89.7%).

Example 7

Addition of Methyl Formate to Methyl Norbornene Dicarboxylate

The reaction was carried out under the same conditions as in Example 3, except that 2.0 mmol of N-methylpyrrolidine as a basic compound and 0.5 mmol of dichloromethane as an organic halogen compound were added to the catalyst system used in Example 3. The reaction mixture thus obtained was analyzed by gas chromatography, and the amount of methyl norbornane-2,3,5-tricarboxylate produced by the reaction was 8.64 mmol (yield in terms of methyl 5-norbornene-2,3-dicarboxylate 86.4%).

Example 8

Polymerization of Methyl Formate to Methyl Norbornene Dicarboxylate

The reaction was carried out all under the same conditions as in Example 6, except that 0.5 mmol of trioctylmethylammonium chloride as a halide salt and 2.0 mmol of triethylamine as a basic compound were added to the catalyst system of Example 6. The reaction mixture thus obtained was analyzed by gas chromatography, and the amount of methyl norbornane-2,3,5-tricarboxylate produced by the reaction was 9.03 mmol (yield in terms of methyl 5-norbornene-2,3-dicarboxylate 90.3%).

Comparative Example 4

Catalyst System Consisting of Ruthenium Compound and Halide Salt Only

The reaction was carried out all under the same conditions as in Example 3, except that the cobalt compound used in the catalyst system of Example 3 was not used. The reaction mixture thus obtained was analyzed by gas chromatography, and only a trace amount of methyl norbornane-2,3,5-tricarboxylate was produced by the reaction.

Comparative Example 5

Catalyst System Consisting of Cobalt Compound and Halide Salt Only

The reaction was carried out all under the same conditions as in Example 3, except that the ruthenium compound used in the catalyst system of Example 3 was not used. The reaction mixture thus obtained was analyzed by gas chromatography, and only a trace amount of methyl norbornane-2,3,5-tricarboxylate was produced by the reaction.

Comparative Example 6

Catalyst System Consisting of Ruthenium Compound and Cobalt Compound Only

The reaction was carried out all under the same conditions as in Example 3, except that the halide salt used in the catalyst system of Example 3 was not used. The reaction mixture thus obtained was analyzed by gas chromatography, and only a trace amount of methyl norbornane-2,3,5-tricarboxylate was produced by the reaction.

Example 9

Polymerization of Methyl Formate to Methyl Norbornene Dicarboxylate

The reaction was carried out all under the same conditions as in Example 8, except that the ruthenium compound [Ru(CO)$_2$Cl$_2$]$_n$ produced in advance using RuCl$_3$ and formic acid according to the method described in M. J. Cleare, W. P. Griffith, J. Chem. Soc. (A), 1969, 372 (Non-Patent Literature 5), was used in an amount of 0.05 mmol in terms of Ru metal. The reaction mixture thus obtained was analyzed by gas chromatography, and the amount of methyl norbornane-2,3,5-tricarboxylate produced by the reaction was 8.59 mmol (yield in terms of methyl 5-norbornene-2,3-dicarboxylate 85.9%).

Example 10

Addition of Methyl Formate to Methyl Norbornene Dicarboxylate

The reaction was carried out all under the same conditions as in Example 8, except that 0.025 mmol of cobalt citrate dihydrate was used as the cobalt compound for the catalyst system of Example 8. The reaction mixture thus obtained was analyzed by gas chromatography, and the amount of methyl norbornane-2,3,5-tricarboxylate produced by the reaction was 8.78 mmol (yield in terms of methyl 5-norbornene-2,3-dicarboxylate 87.8%).

Example 11

Addition of Methyl Formate to Methyl Norbornene Dicarboxylate

The reaction was carried out all under the same conditions as in Example 6, except that 0.05 mmol of cobalt acetate tetrahydrate was used as the cobalt compound for the catalyst system of Example 6. The reaction mixture thus obtained was analyzed by gas chromatography, and the amount of methyl norbornane-2,3,5-tricarboxylate produced by the reaction was 8.42 mmol (yield in terms of methyl 5-norbornene-2,3-dicarboxylate 84.2%).

Example 12

Addition of Methyl Formate to Norbornene

In a pressure reactor made of stainless steel and having an internal volume of 50 ml, 0.05 mmol of $[Ru(CO)_3Cl_2]_2$ as a ruthenium compound, 0.05 mmol of $Co_2(CO)_8$ as a cobalt compound, and 0.25 mmol of butylmethylpyrrolidinium chloride as a halide salt were introduced and mixed at room temperature, and thus a catalyst system was obtained. 5.0 mmol of norbornene and 5.0 mL of methyl formate were added to this catalyst system, subsequently the reactor was purged with nitrogen gas at 0.5 MPa, and the system was maintained for 15 hours at 120° C. Thereafter, the reactor was cooled to room temperature, and the pressure was released. A portion of the remaining organic phase was withdrawn, and the components of the reaction mixture were analyzed by using gas chromatography. According to the analysis results, the amount of methyl norbornane monocarboxylate produced by the reaction was 7.07 mmol (yield in terms of norbornene 70.7%).

Example 13

Addition of Methyl Formate to Norbornene

The reaction was carried out all under the same conditions as in Example 12, except that 0.05 mmol of $Ru_3(CO)_{12}$ was used as the ruthenium compound for the catalyst system of Example 12. The components of the reaction mixture were analyzed in the same manner as in Example 12, and the amount of methyl norbornane monocarboxylate produced by the reaction was 1.09 mmol (yield in terms of norbornene 10.9%).

Example 14

Addition of Methyl Formate to Norbornene

The reaction was carried out all under the same conditions as in Example 12, except that 0.05 mmol of $RuCl_3.3H_2O$ was used as the ruthenium compound for the catalyst system of Example 12. The components of the reaction mixture were analyzed in the same manner as in Example 12, and the amount of methyl norbornane monocarboxylate produced by the reaction was 2.67 mmol (yield in terms of norbornene 26.7%).

Example 15

Addition of Methyl Formate to Norbornene

The reaction was carried out all under the same conditions as in Example 12, except that 0.05 mmol of $RuI_3$ was used as the ruthenium compound for the catalyst system of Example 12. The components of the reaction mixture were analyzed in the same manner as in Example 12, and the amount of methyl norbornane monocarboxylate produced by the reaction was 3.24 mmol (yield in terms of norbornene 32.4%).

Example 16

Addition of Methyl Formate to Norbornene

The reaction was carried out all under the same conditions as in Example 12, except that 0.05 mmol of $[RuCl_2(cod)]_2$ was used as the ruthenium compound for the catalyst system of Example 12. The components of the reaction mixture were analyzed in the same manner as in Example 12, and the amount of methyl norbornane monocarboxylate produced by the reaction was 8.82 mmol (yield in terms of norbornene 88.2%).

Example 17

Addition of Methyl Formate to Norbornene

In a pressure reactor made of stainless steel and having an internal volume of 50 ml, 0.025 mmol of $[Ru(CO)_3Cl_2]_2$ as a ruthenium compound, 0.025 mmol of $Co_2(CO)_8$ as a cobalt compound, 0.25 mmol of trioctylammonium chloride as a halide salt, 2.0 mmol of triethylamine as a basic compound, 0.25 mmol of p-cresol as a phenolic compound, and 0.25 mmol of dichloromethane as an organic halide were introduced and mixed at room temperature, and thus a catalyst system was obtained. 5.0 mmol of norbornene and 5.0 mL of methyl formate were added to this catalyst system, subsequently the reactor was purged with nitrogen gas at 0.5 MPa, and the system was maintained for 15 hours at 120° C. Thereafter, the reactor was cooled to room temperature, and the pressure was released. A portion of the remaining organic phase was withdrawn, and the components of the reaction mixture were analyzed by using gas chromatography. According to the analysis results, the amount of methyl norbornane monocarboxylate produced by the reaction was 8.60 mmol (yield in terms of norbornene 86.0%).

Comparative Example 7

Addition of Methyl Formate to Norbornene

In a pressure reactor made of stainless steel and having an internal volume of 50 ml, 0.05 mmol of $[Ru(CO)_3Cl_2]_2$ as a ruthenium compound, 0.05 mmol of $Co_2(CO)_8$ as a cobalt compound, and 1.0 mmol of butylmethylpyrrolidinium chloride as a halide salt were introduced and mixed at room temperature, and thus a catalyst system was obtained. 5.0 mmol of norbornene and 515.0 mmol of methanol were added to this catalyst system, subsequently carbon monoxide gas was injected into the reactor to 5 MPa, and the system was maintained for 15 hours at 120° C. Thereafter, the reactor was cooled to room temperature, and the pressure was released. A portion of the remaining organic phase was withdrawn, and the components of the reaction mixture were analyzed by using gas chromatography. According to the analysis results, only a trace amount of methyl norbornane monocarboxylate was produced by the reaction.

The results obtained in Examples 1 to 17 and Comparative Examples 1 to 7 are summarized in Table 1.

TABLE 1

Results of Examples 1~17 and Comparative Examples 1~7

| | Unsaturated compound/formic acid ester | Ru Compound | Co Compound | Halide salt | Basic compound | Phenolic compound | Organic halogen compound | Yield of product |
|---|---|---|---|---|---|---|---|---|
| Example 1 | Ethylene/ Methyl formate | $[Ru(CO)_3Cl_2]_2$ | $Co_2(CO)_8$ | [bmpy]Cl | None | None | None | 242 equivalent (in terms of Ru atom) |
| Example 2 | Cyclohexene/ Methyl formate | $[Ru(CO)_3Cl_2]_2$ | $Co_2(CO)_8$ | $[(Ph_3P)2N]I$ | None | None | None | 49.4% |
| Example 3 | NBDAC-M/ Methyl formate | $[Ru(CO)_3Cl_2]_2$ | $Co_2(CO)_8$ | [bmpy]Cl | None | None | None | 8.4% |
| Example 4 | NBDAC-M/ Methyl formate | $[Ru(CO)_3Cl_2]_2$ | $Co_2(CO)_8$ | [bmpy]Cl | N-methylpyrrolidine | None | None | 11.1% |
| Example 5 | NBDAC-M/ Methyl formate | $[Ru(CO)_3Cl_2]_2$ | $Co_2(CO)_8$ | [bmpy]Cl | tBuONa | None | None | 30.8% |
| Example 6 | NBDAC-M/ Methyl formate | $[Ru(CO)_3Cl_2]_2$ | $Co_2(CO)_8$ | [bmpy]Cl | N-methylpyrrolidine | p-cresol | None | 89.7% |
| Example 7 | NBDAC-M/ Methyl formate | $[Ru(CO)_3Cl_2]_2$ | $Co_2(CO)_8$ | [bmpy]Cl | N-methylpyrrolidine | None | $CH_2Cl_2$ | 86.4% |
| Example 8 | NBDAC-M/ Methyl formate | $[Ru(CO)_3Cl_2]_2$ | $Co_2(CO)_8$ | [bmpy]Cl/ $[MeN(Oct)_3]Cl$ | N-methylpyrrolidine/ TEA | p-cresol | None | 90.3% |
| Example 9 | NBDAC-M/ Methyl formate | $[Ru(CO)_2Cl_2]n$ | $Co_2(CO)_8$ | [bmpy]Cl/ $[MeN(Oct)_3]Cl$ | N-methylpyrrolidine/ TEA | p-cresol | None | 85.9% |
| Example 10 | NBDAC-M/ Methyl formate | $[Ru(CO)_3Cl_2]_2$ | Cobalt citrate dihydrate | [bmpy]Cl/ $[MeN(Oct)_3]Cl$ | N-methylpyrrolidine/ TEA | p-cresol | None | 87.8% |
| Example 11 | NBDAC-M/ Methyl formate | $[Ru(CO)_3Cl_2]_2$ | Cobalt acetate tetrahydrate | [bmpy]Cl | N-methylpyrrolidine | p-cresol | None | 84.2% |
| Example 12 | NB/ Methyl formate | $[Ru(CO)_3Cl_2]_2$ | $Co_2(CO)_8$ | [bmpy]Cl | None | None | None | 70.7% |
| Example 13 | NB/ Methyl formate | $Ru_3(CO)_{12}$ | $Co_2(CO)_8$ | [bmpy]Cl | None | None | None | 10.9% |
| Example 14 | NB/ Methyl formate | $RuCl_3 \cdot 3H_2O$ | $Co_2(CO)_8$ | [bmpy]Cl | None | None | None | 26.7% |
| Example 15 | NB/ Methyl formate | $RuI_3$ | $Co_2(CO)_8$ | [bmpy]Cl | None | None | None | 32.4% |
| Example 16 | NB/ Methyl formate | $[RuCl_2(cod)]_2$ | $Co_2(CO)_8$ | [bmpy]Cl | None | None | None | 88.2% |
| Example 17 | NB/ Methyl formate | $[Ru(CO)_3Cl_2]_2$ | $Co_2(CO)_8$ | $[MeN(Oct)_3]Cl$ | TEA | p-cresol | $CH_2Cl_2$ | 86.0% |
| Comparative Example 1 | Ethylene/ Methyl formate | $[Ru(CO)_3Cl_2]_2$ | None | [bmpy]Cl | None | None | None | 81 equivalent (in terms of Ru atom) |
| Comparative Example 2 | Ethylene/ Methyl formate | None | $Co_2(CO)_8$ | [bmpy]Cl | None | None | None | A trace amount |
| Comparative Example 3 | Ethylene/ Methyl formate | $[Ru(CO)_3Cl_2]_2$ | $Co_2(CO)_8$ | None | None | None | None | A trace amount |
| Comparative Example 4 | NBDAC-M/ Methyl formate | $[Ru(CO)_3Cl_2]_2$ | None | [bmpy]Cl | None | None | None | A trace amount |
| Comparative Example 5 | NBDAC-M/ Methyl formate | None | $Co_2(CO)_8$ | [bmpy]Cl | None | None | None | A trace amount |
| Comparative Example 6 | NBDAC-M/ Methyl formate | $[Ru(CO)_3Cl_2]_2$ | $Co_2(CO)_8$ | None | None | None | None | A trace amount |
| Comparative Example 7 | $NB/CH_3OH/CO$ | $[Ru(CO)_3Cl_2]_2$ | $Co_2(CO)_8$ | [bmpy]Cl | None | None | None | A trace amount |

Annotation:
(1) NBDAC-M: Methyl 5-norbornene-2,3-dicarboxylate (a product that had been synthesized in advance according to a well known method was used)
(2) $[Ru(CO)_3Cl_2]_2$ (Strem Chemicals, Inc.)
(3) $Co_2(CO)_8$ (Tokyo Chemical Industry Co., Ltd.)
(4) [bmpy]Cl: Butylmethylpyrrolidium chloride (Tokyo Chemical Industry Co., Ltd.)
(5) $[(Ph3P)2N]I$: [Bis(triphenylphosphine)iminium] iodide (Tokyo Chemical Industry Co., Ltd.)
(6) tBuONa: Sodium t-butoxide (Tokyo Chemical Industry Co., Ltd.)
(7) N-methylpyrrolidine: (Tokyo Chemical Industry Co., Ltd.)
(8) [MeN(Oct)3]Cl: Trioctylmethylammonium chloride (Tokyo Chemical Industry Co., Ltd.)
(9) TEA: Triethylamine (Wako Pure Chemical Industries, Ltd.)
(10) $CH_2Cl_2$: Dichloromethane (Tokyo Chemical Industry Co., Ltd.)
(11) Cobalt citrate dihydrate (Alfa Aesar)
(12) Cobalt acetate tetrahydrate (Tokyo Chemical Industry Co., Ltd.)
(13) NB: Norbornene (= bicyclo[2,2,1]hepta-2-ene) (Sigma-Aldrich Co. LLC)
(14) $Ru_3(CO)_{12}$ (Sigma-Aldrich Co. LLC)
(15) $RuCl_3 \cdot 3H_2O$ (Strem Chemicals, Inc.)
(16) $RuI_3$ (Sigma-Aldrich Co. LLC)
(17) $[RuCl_2(cod)]_2$ (Sigma-Aldrich Co. LLC)

As is obvious from the results of Example 1 and Comparative Examples 1 to 3, it can be seen that in the production method of the present invention, the use of a particular catalyst system combining a ruthenium compound, a cobalt compound and halide salt is indispensable, and such a particular catalyst system allows efficient production of an ester compound which is ethylene combined with methyl formate, even at a reaction temperature of about 120° C.

Furthermore, as is obvious from the results of Examples 2 to 17 and Comparative Examples 4 to 6, it can be seen that when a particular catalyst system combining a ruthenium compound, a cobalt compound and a halide salt is used, esterification reactions of various unsaturated organic compounds can be accelerated. Also, it can be seen that when a ruthenium complex which combines a carbonyl ligand and a halogen ligand in the molecule is used as a ruthenium compound, there is a tendency that a more effective catalytic effect is obtained. It can also be seen that when at least one of a basic compound, a phenolic compound and an organic halide is added to the catalyst system as necessary, the reaction can be more effectively accelerated.

Furthermore, as is obvious from the results of Comparative Example 7, it can be seen that the catalyst system according to the present invention does not act on a carbon monoxide/methanol system. That is, it is speculated that when the catalyst system according to the present invention is used, an esterification reaction proceeds not as a result of the decomposition of methyl formate into carbon monoxide/methanol, but there is adopted a mechanism in which a hydroesterification reaction proceeds as a result of the cleavage of the C—H bond of methyl formate, and such a series of reactions are promoted by the particular combination of catalysts.

The invention claimed is:

1. A method for producing an ester compound, the method comprising the step of reacting an organic compound having at least one unsaturated carbon bond in the molecule, and a formic acid ester in the presence of a catalyst system containing: a ruthenium compound; a cobalt compound; a halide salt; and a phenolic compound.

2. The method according to claim 1, wherein the ruthenium compound is a ruthenium complex having both a carbonyl ligand and a halogen ligand in the molecule.

3. The method according to claim 1, wherein the cobalt compound is a cobalt complex having a carbonyl ligand in the molecule.

4. The method according to claim 1, wherein the halide salt is a quaternary ammonium salt.

5. The method according to claim 1, wherein the reaction is carried out in the presence of a basic compound.

6. The method according to claim 5, wherein the basic compound is a tertiary amine compound.

7. The method according to claim 1, wherein the reaction is carried out in the presence of an organic halogen compound.

8. The method according to claim 1, wherein the ruthenium compound is contained in an amount in a range of 1/10000 to 1 equivalent based on the organic compound having at least one unsaturated carbon bond in the molecule.

9. The method according to claim 1, wherein the ruthenium compound is contained in an amount in a range of 1/1000 to 1/50 equivalents based on the organic compound having at least one unsaturated carbon bond in the molecule.

10. The method according to claim 1, wherein the cobalt compound is contained in an amount in a range of 1/100 to 10 equivalents based on the ruthenium compound.

11. The method according to claim 1, wherein the cobalt compound is contained in an amount in a range of 1/10 to 5 equivalents based on the ruthenium compound.

12. The method according to claim 1, wherein the halide salt is contained in an amount in a range of 1 to 1000 equivalents based on the ruthenium compound.

13. The method according to claim 1, wherein the halide salt is contained in an amount in a range of 2 to 50 equivalents based on the ruthenium compound.

14. The method according to claim 1, wherein the ruthenium compound is contained in an amount in a range of 1/10000 to 1 equivalent based on the organic compound having at least one unsaturated carbon bond in the molecule, the cobalt compound is contained in an amount in a range of 1/100 to 10 equivalents based on the ruthenium compound, and the halide salt is contained in an amount in a range of 1 to 1000 equivalents based on the ruthenium compound.

15. The method according to claim 1, wherein the ruthenium compound is contained in an amount in a range of 1/1000 to 1/50 equivalents based on the organic compound having at least one unsaturated carbon bond in the molecule, the cobalt compound is contained in an amount in a range of 1/10 to 5 equivalents based on the ruthenium compound, and the halide salt is contained in an amount in a range of 2 to 50 equivalents based on the ruthenium compound.

16. The method according to claim 1, wherein the step of reacting the organic compound having at least one unsaturated carbon bond in the molecule, and the formic acid ester in the presence of a catalyst system is carried out at a temperature in a range of 80° C. to 200° C.

17. The method according to claim 1, wherein the step of reacting the organic compound having at least one unsaturated carbon bond in the molecule, and the formic acid ester in the presence of a catalyst system is carried out at a temperature in a range of 100° C. to 160° C.

* * * * *